United States Patent
Diamond et al.

(10) Patent No.: US 7,846,321 B2
(45) Date of Patent: *Dec. 7, 2010

(54) ERROR DETECTION IN ANALYTE MEASUREMENTS BASED ON MEASUREMENT OF SYSTEM RESISTANCE

(75) Inventors: Steven Diamond, Somerville, MA (US); Ian Harding, Somerville, MA (US); Richard Williams, Andover, MA (US)

(73) Assignee: Agamatrix, Inc., Salem, NH (US)

( * ) Notice: Subject to any disclaimer, the term of this patent is extended or adjusted under 35 U.S.C. 154(b) by 421 days.

This patent is subject to a terminal disclaimer.

(21) Appl. No.: 11/874,766

(22) Filed: Oct. 18, 2007

(65) Prior Publication Data

US 2008/0093227 A1    Apr. 24, 2008

Related U.S. Application Data

(60) Provisional application No. 60/862,002, filed on Oct. 18, 2006.

(51) Int. Cl.
    C12Q 1/00    (2006.01)
    C12M 1/00    (2006.01)
(52) U.S. Cl. .............. 205/778; 204/403.01; 204/403.11
(58) Field of Classification Search .......... 435/4–40.52, 435/287.1–288.7; 324/691–724; 702/19–26, 702/85–107; 205/777.5, 778, 792; 600/345–348; 422/68.1–98; 436/62–71, 500–548; 204/403.01–403.15
See application file for complete search history.

(56) References Cited

U.S. PATENT DOCUMENTS

| | | | |
|---|---|---|---|
| 5,243,516 A | 9/1993 | White | |
| 5,266,179 A | 11/1993 | Nankai et al. | |
| 5,320,732 A | 6/1994 | Nankai et al. | |
| 5,352,351 A | 10/1994 | White et al. | |
| 5,438,271 A | 8/1995 | White et al. | |
| 5,942,102 A | 8/1999 | Hodges et al. | |
| 6,284,125 B1 | 9/2001 | Hodges et al. | |
| 6,365,033 B1 | 4/2002 | Graham et al. | |
| 6,616,819 B1 | 9/2003 | Liamos et al. | |
| 7,517,439 B2 * | 4/2009 | Harding et al. | ............. 204/401 |
| 2002/0130674 A1 | 9/2002 | Lagowski et al. | |

(Continued)

FOREIGN PATENT DOCUMENTS

JP    2001066274    3/2001

(Continued)

OTHER PUBLICATIONS

Matsumoto et al. "Fundamental Studies of Glucose Oxidase Deposition on a Pt Electrode", Anal. Chem., Jan. 15, 2002, pp. 362-367, vol. 74, No. 2.

*Primary Examiner*—Nam X Nguyen
*Assistant Examiner*—Susan Thai
(74) *Attorney, Agent, or Firm*—Larson & Anderson, LLC

(57) ABSTRACT

Measurement of the series track resistance of a working and counter electrode pair in an electrochemical test strip provide error detection for multiple variations in the quality of the test strip, as well as the operation of strip in the test meter. In particular, a single measurement of series resistance can be used to detect and generate an error message when an incorrect reading is likely to result due to (1) damaged electrode tracks, (2) fouled electrode surfaces, (3) dirty strip contacts, or (4) short circuit between the electrodes.

10 Claims, 10 Drawing Sheets

U.S. PATENT DOCUMENTS

| | | | |
|---|---|---|---|
| 2004/0157337 A1 * | 8/2004 | Burke et al. | 436/70 |
| 2005/0109637 A1 | 5/2005 | Iyengar et al. | |
| 2005/0265094 A1 | 12/2005 | Harding et al. | |
| 2005/0279631 A1 | 12/2005 | Celentano | |
| 2005/0284758 A1 | 12/2005 | Funke et al. | |
| 2006/0231423 A1 | 10/2006 | Harding et al. | |
| 2006/0231424 A1 | 10/2006 | Harding et al. | |

FOREIGN PATENT DOCUMENTS

| | | |
|---|---|---|
| JP | 2004233294 | 8/2004 |
| WO | 2005022143 A2 | 3/2005 |

\* cited by examiner

ERROR DETECTION IN ANALYTE MEASUREMENTS BASED ON MEASUREMENT OF SYSTEM RESISTANCE

STATEMENT OF RELATED APPLICATIONS

This application claims the benefit of US Provisional Application No. 60/862,002 filed Oct. 18, 2006. This application is related to U.S. patent application Ser. No. 10/907,817, filed Apr. 15, 2005, now US Patent Publication No. US 2006-0231424 A1. Both applications are incorporated herein by reference in their entirety.

BACKGROUND OF THE INVENTION

This application relates to error correction methods for use in electrochemical determination of analytes such as glucose, and to a meter, and meter-test strip combination for use in such a method.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

Electrochemical detection of glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produced a reduced mediator. Reduced mediator is oxidized at one of the electrodes, and then diffuses back to either be reduced at the other electrode or by the reduced enzyme to complete the cycle, and to result in a measurable current. The measured current is related to the amount of glucose in the sample, and various techniques are known for determining glucose concentrations in such a system are known. (See, U.S. Pat. Nos. 6,284,125; 5,942,102; 5,352,351; and 5,243,516, which are incorporated herein by reference.)

It is generally desirable in electrochemical test strips to utilize a small volume sample. Because these tests may be performed with considerable frequency, it is desirable to utilize disposable, single use test strips and to minimize the per strip cost. These desires favor less precise manufacturing methods. At the same time, there is a conflicting desire for use of the smallest possible sample volume, and determinations of sufficient accuracy and precision to be useful. It would therefore be useful to be able to make corrections for multiple variations in the quality of the strip based on measurements made at the time of use, or to reject strips that are too far outside acceptable parameters. It would further be desirable to make these corrections or to reject strips based upon one or at most a small number of measured parameters.

SUMMARY OF THE INVENTION

The present invention makes use of a measure of the series resistance of a working and counter electrode pair in an electrochemical test strip to provide correction values for multiple variations in the quality of the test strip, as well as the operation of strip in the test meter. In particular, in accordance with the invention a single measurement of series resistance can be used to detect and generate an error message when an incorrect reading is likely to result due to (1) damaged electrode tracks, (2) fouled electrode surfaces, (3) dirty strip contacts, or (4) short circuit between the electrodes.

In accordance with the method of the present invention, determination of an analyte such as glucose in a sample such as blood is achieved by the steps of:

(a) introducing sample to an electrochemical test strip having working and counter electrodes;

(b) applying a potential difference, $V_{app}$, between the electrodes of the test strip and observing a current signal sufficient to provide a determination of analyte in the sample and for a period of time sufficient to determine a pre-switching current, $I_{pre-switch}$;

(c) switching off the applied potential at time $t_{switch}$ and determining the magnitude, $V_{drop}$, of the immediate voltage drop, if any;

(d) calculating a track resistance $R_{track}$ and comparing the determined magnitude of $R_{track}$, against a predetermined range, and rejecting the test if the magnitude of $R_{track}$ falls outside of the range wherein the value of $R_{track} = V_{drop}/I_{pre-switch}$, and (e) if the magnitude is within the predetermined range, proceeding to display or communicate the result from the determination of analyte.

The invention also provides a meter which is adapted to provide evaluate series electrode resistance and provide an error message where it is outside of a predetermined range.

In a further aspect, the invention provides a measurement system comprising a meter which is adapted to evaluate series electrode resistance and provide an error message where it is outside of a predetermined range in combination with an electrochemical test strip.

DETAILED DESCRIPTION OF THE INVENTION

I. DEFINITIONS

Figure 1:
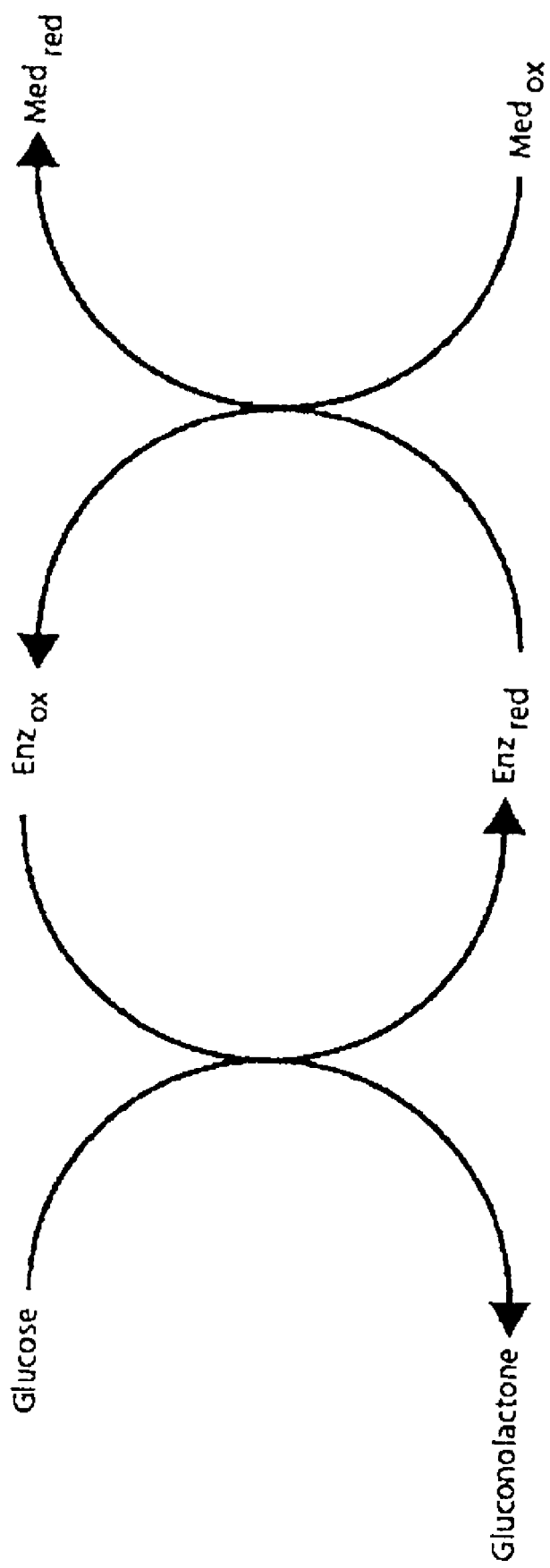
FIG. 1 shows the electron transfer reactions that occur in a conventional amperometric glucose detector.

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment.

(b) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(c) "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

(d) "facing electrodes" are a pair of electrodes disposed parallel to but in a separate plane from each other. Some or all of the opposed surfaces of a pair of facing electrodes overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes.

(e) "predetermined amount" is used in this application to refer to amounts that are determined empirically for a particular meter or test strip or meter/strip combination. The predetermined amounts will reflect an optimization for the needs of the user, taking into account the confidence levels needed, and need not achieve the best possible results or 100% accuracy.

(f) "switching off" of the applied potential refers to the creation of an open circuit that forces the current to be zero (by opening a switch or introducing a high impedance into the circuit) that allows a built-up chemical concentration gradient and ion adsorption in the double layer to determine the potential between the electrodes. This is not the same thing as setting the voltage to zero volts.

(g) "series electrode resistance" causes a difference between the applied voltage, and the actual voltage perceived by the electrochemistry at the electrode. Electrode resistance arises as a result of the resistance of the electrode material and the connectors associated with the electrodes, fouling of the electrode and similar factors.

(h) $V_{drop}$ is the difference between the applied voltage and the actual voltage at the electrode that arises as a result of series electrode resistance. $V_{drop-avg}$ is a numerical average of a plurality of measured $V_{drop}$ values determined in a plurality of switching cycles.

(i) "mediator" refers to a chemical species that is electrochemically detected. Numerous electron transfer mediators suitable for detection of analytes such as glucose are known, and include without limitation iron, ruthenium, and osmium compounds. In some embodiments of the invention, the mediator is produced through one or more reaction steps and is related to the concentration of the actual analyte, such as glucose. The present invention is also applicable, however, to circumstances in which the detected chemical species is the reduced form of the analyte to be detected, and this is also an embodiment of the invention.

(j) "$I_{pre-switch}$" refers to a current value determined prior to the switching off of the applied potential. The time at which this current measurement is taken is sufficiently close in time to the time $t_{switch}$ that it is representative of current at the actual time of the switching. As will be apparent, the amount of time that the current measurement can be made prior $t_{switch}$ is dependent on the rate of change of the current at this time, with longer times being acceptable if the switch is made in the plateau region, and shorter times being required when the value of current is rapidly changing.

Numerical values in the specification and claims of this application should be understood to include numerical values which are the same when reduced to the same number of significant figures and numerical values which differ from the stated value by less than the experimental error of the technique used to measure the value.

II. DETECTION OF ANALYTE, FOR EXAMPLE GLUCOSE

Figure 2:
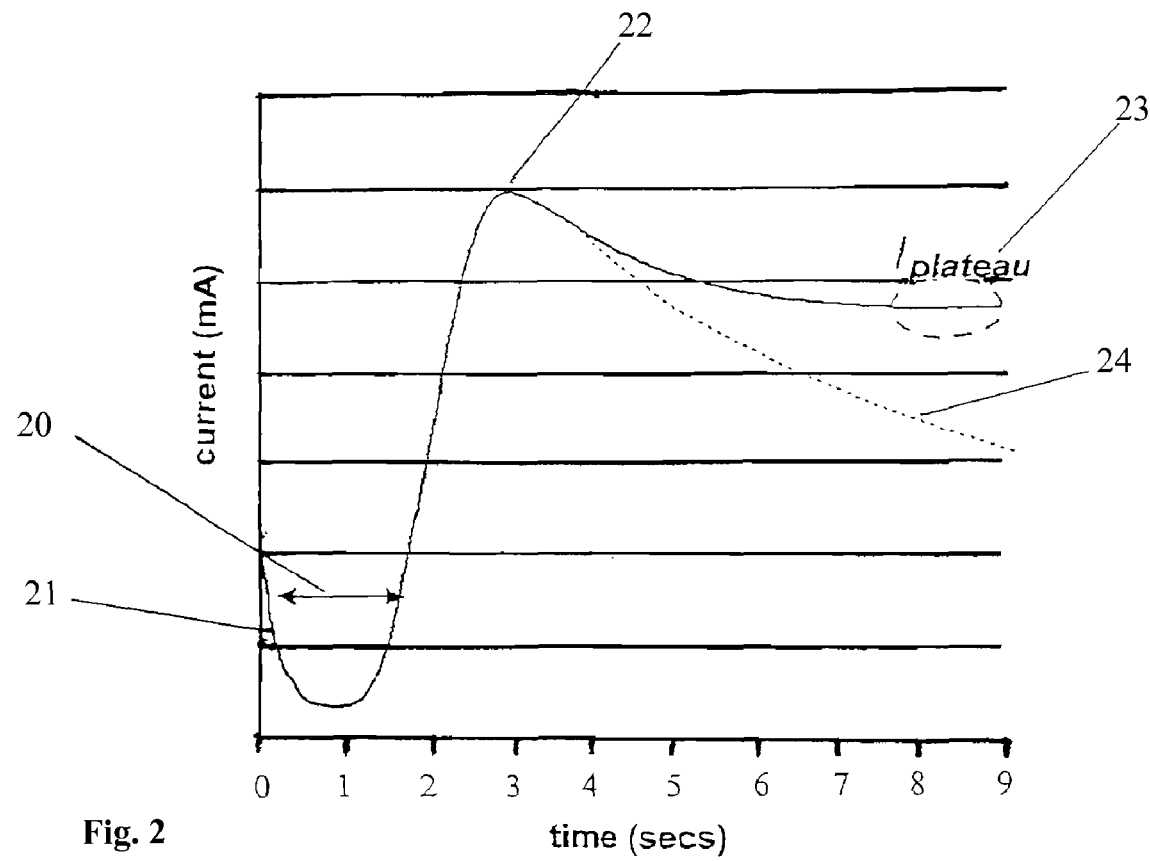
FIG. 2 show the type of current versus time profiles observed in two different electrochemical test strip configurations.

FIG. 2 shows current versus time profiles observed in two different electrochemical test strip configurations, one with facing electrodes and one with side-by-side electrodes, where the electrochemical reagents are initially disposed only on the working electrode, and not on the counter electrode. In both cases, the current trace shows an immediate initial current 21 on the time scale shown following application of the potential. This current is associated with the initial charging of the double layer at the surface of the electrodes. Thereafter, the current decreases, because current is dependent on the mediator diffusing from the working electrode to the counter electrode. The duration of this reduced current (indicated by arrow 20) is dependent on the distance between the electrodes, and on the mobility of the mediator. Mediator mobility is a property of the mediator itself, i.e., the diffusion coefficient, but is also dependent on other sample properties such as hematocrit and viscosity. After the period of reduced current 20, the current rapidly rises to a peak current 22. In the case of facing electrodes, the current declines to a plateau current 23 ($I_{plateau}$) which reflects the recycling or shuttling of mediator between the electrodes. In the case of side-by-side electrodes, the current continues to decay in the time scale indicated, as indicated by dashed line 24. At longer times, this curve 24 may also shows effects of recycling/shuttling of mediator if the electrodes are close enough together.

In the region of the decay following the peak, before recycling becomes dominant, the current decay can be modeled by the Cottrell equation, i.e., $$1/I^2 \propto t$$

where I is the current and t is time. Cottrell analysis can be utilized to determine glucose concentration as described in U.S. Pat. Nos. 5,243,516; 5,352,351 and 6,284,125. Commonly assigned U.S. patent application Ser. No. 10/907,803, filed Apr. 15, 2005, which is incorporated herein by reference, discloses a Cottrell analysis of analyte concentration that includes a mobility correction obtained when the applied potential is switched off after monitoring the current to obtain data for determination of analyte.

As an alternative to Cottrell analysis, current in the plateau region 23 of FIG. 2 can be used to determine analyte concentration. This type of measurement is particularly applicable when using conduction cell test strips, as described in commonly assigned U.S. patent application Ser. No. 10/924,510, which is incorporated herein by reference.

In determining the numerical value of analyte concentration which is communicated/displayed to a user, one or more correction factors based on calibration values for a lot of strips, or measurements made during the analysis may be applied. Further, it will be understood that a look up table or other conversion system may be used to convert a raw value into a meaningful value for communication/display to the user.

III. DETERMINATION OF $V_{drop}$

After sufficient information is collected to make a determination of analyte, the applied potential is switched off at time $t_{switch}$. At this point in time, there remains a potential difference between the electrodes as a result of a chemical potential gradient. In the absence of resistance, this potential would decay with a time constant determined by the mobility of the mediator in the system. However, when the actual voltage profile of an electrochemical strip with carbon electrodes or other sources of resistance is measured, an immediate drop in voltage is observed after the applied potential is switched off. The magnitude of this drop, $V_{drop}$ is a function of several factors, including the resistance of the electrode material and the connectors associated with the electrodes, fouling of the electrode and similar factors. Thus, the drop is larger with carbon electrodes than with a low resistance electrode such as one made of gold, but may still be present regardless of the electrode material of other sources of series resistance are present.

The magnitude of $V_{drop}$ is determined by observing the potential differences between the electrodes after $t_{switch}$. The decrease in potential is essentially immediate, i.e, it occurs within about the first 1 millisecond after $t_{Switch}$. Thus, in one embodiment of the invention, $V_{drop}$ can be approximated as the difference between the application voltage, $V_{app}$, and the voltage measured some very short interval after $t_{switch}$ for example at 1 milliseconds after $t_{switch}$. This approach is not ideal, however, because the potential difference continues to decrease, albeit at a slower rate, after the immediate voltage has occurred, and the rate of this further decrease is sample dependent. This, plus the fact that only one instantaneous value is used means that the determination in $V_{drop}$ in this way is subject to error that may be significant and not reproducible.

Figure 3:
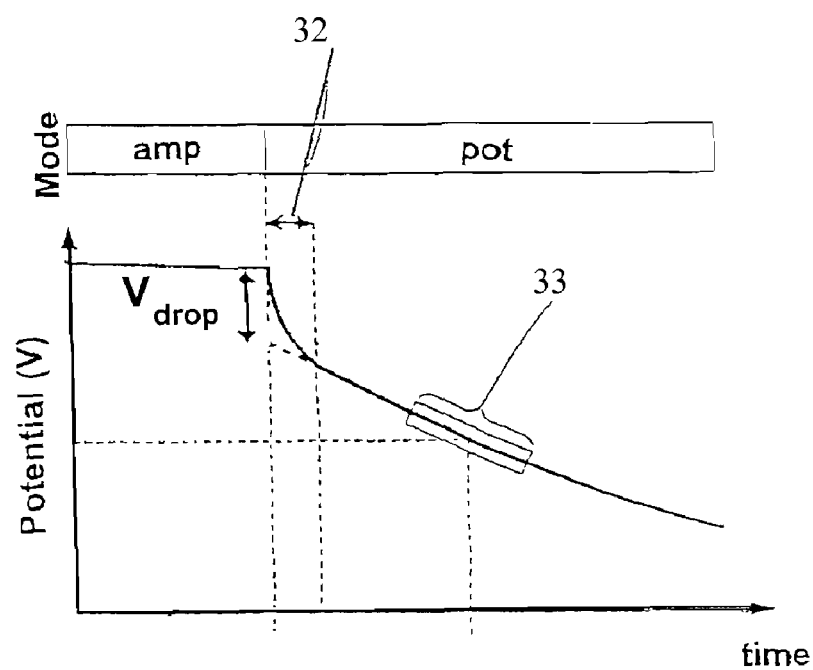
FIG. 3 shows the variation of potential as a function of time, when the applied potential used during amperometric mode is switched off, and potentiometric measurements are made.

A preferred method for determining $V_{drop}$ therefore is based on potential measurements made substantially after $V_{drop}$ has occurred. FIG. 3 shows the variation of potential as a function of time, when the applied potential used during amperometric mode (amp) is switched off, and potentiometric measurements (pot mode) are made. The interval 32 is a predetermined time which is selected such that the decrease in voltage as a result of resistance has occurred, and that subsequent voltage decreases are reasonably fit to a linear model. In some embodiments of the invention, the interval 32 is from 0.5 to 2 milliseconds, for example 1 millisecond.

After the interval 32 has passed, data points in the potential versus time plot, for example those in region 33, are fit to a linear model to determine the slope and intercept of the line extrapolated back to $t_{switch}$. A value $V_{elect}$, that is the electrochemical voltage, is determined as the voltage at $t_{switch}$ assuming this straight line extrapolation. $V_{drop}$ is then given by the equation:

$$V_{drop} = V_{app} - V_{elect}.$$

Non-linear fits might also be used if this provides a better model for a particular strip geometry.

Another way to determine $V_{drop}$ is to actually determine $V_{drop}$ in plurality switching cycles, each switching cycle comprising the steps of switching off the applied potential at time $t_{switch}$ and determining the magnitude, $V_{drop}$, of the immediate voltage drop, and then switching the potential back on to prepare for the next switching cycle. As will be apparent in the final switching cycle, the potential need not be switched back on. Thus, the device operates in an alternate series of amperometric and potentiometric modes (amp->pot->amp->pot ... ). The measured values of $V_{drop}$ for each cycle are averaged to produce a value $V_{drop\text{-}avg}$ which can either be used directly for comparison or used in a calculation of track resistance as discussed below. Stated numerically, for n switching cycles $V_{drop\text{-}avg}$ is given by the equation:

$$\frac{1}{n}\left(\sum_n V_{drop,n}\right) = V_{drop\text{-}avg}$$

The use of a plurality of cycles results in improved accuracy since the significance of anomalous readings is reduced by averaging. On the other hand, each cycle takes time, especially if a given device requires time for the current to settle after re-application of the potential, and therefore increases the amount of time it takes to achieve a result for display to a user. The number of cycles used is therefore a compromise between these two factors. In general, suitable numbers of cycles are 2, 3, 4 or 5. The number of cycles may also be determined dynamically based on the observed variance in the switching cycles already evaluated. Thus, if the first two or three cycles produce essentially the same value for $V_{drop}$ it may be dynamically determined that this is a sufficient number of cycles.

IV. ERROR DETECTION USING $V_{drop\text{-}avg}$

In order to detect errors, the determined magnitude of $V_{drop\text{-}avg}$ is checked against a predetermined range, and the test is rejected if the magnitude of $V_{drop\text{-}avg}$ falls outside of the range. In some embodiment of the invention, the predetermined range is open-ended at one end, and thus is equivalent to a single threshold value. In other embodiments of the invention, the predetermined range has both an upper and a lower bound.

Figure 4A:
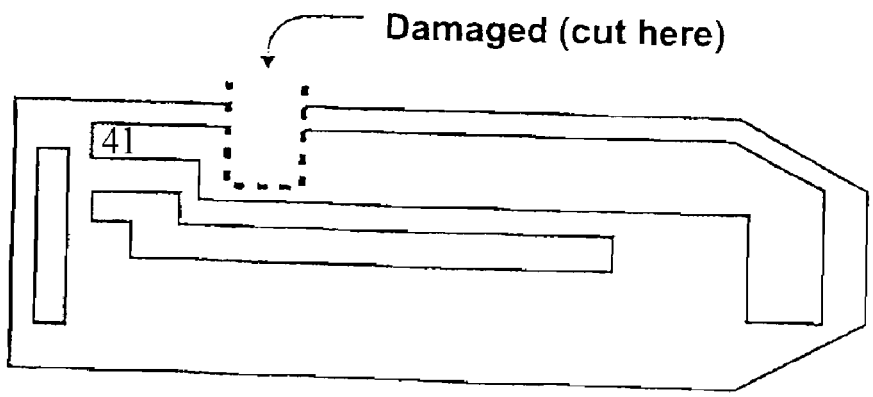
FIGS. 4A and 4B show damage introduced into an electrode test strip, and the variation in $V_{drop}$ measured for damaged and undamaged electrodes.
Figure 4B:
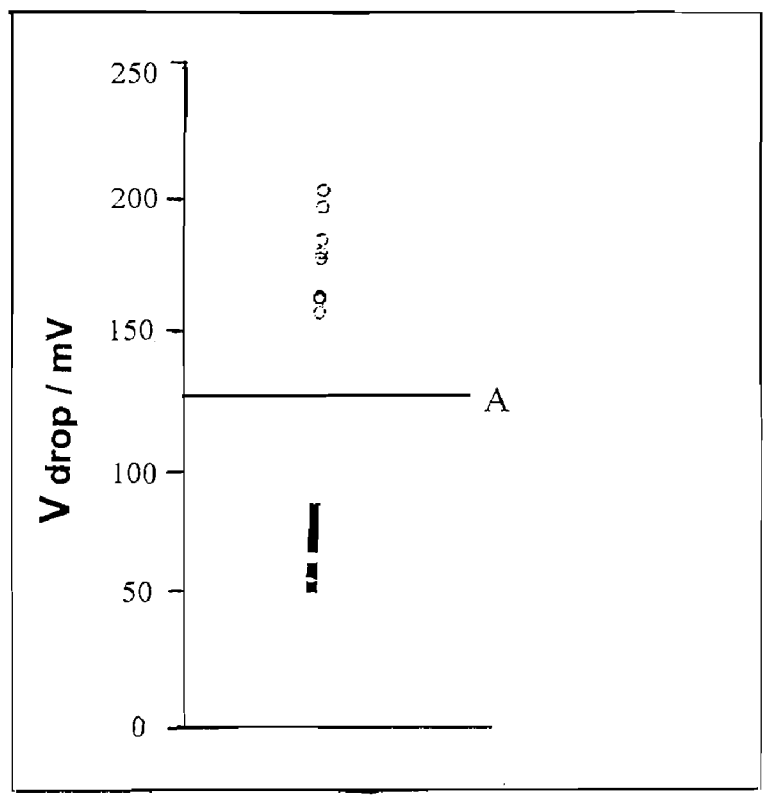

In order to determine appropriate values for the bounds of the predetermined range, a plurality of test strips are tested under conditions that are assumed to exclude error states. These measurements determine the range of normal values that are likely to be encountered. A second set of experiments is then performed in test strips in which errors are intentionally introduced. For example, test trips can be intentionally damaged, for example by scratching the electrode surface; intentionally fouled; the connectors can be intentionally dirtied to create strips that should have higher than normal series electrode resistance, and thus higher values of $V_{drop}$. Finally, a set of experiments that are expected to produce low levels of $V_{drop-avg}$, for example experiments with shorted electrodes, are performed. The values for $V_{drop-avg}$ for each of these sets of experiments are plotted, along a line, and a confidence range or threshold is defined in which most, if not all, of the non-error measurements and substantially none of the error measurements are included within the range. FIG. 4B shows one set of data determined in this way.

V. ERROR DETERMINATION USING $R_{track}$

As an alternative to detection of errors using $V_{drop}$ or $V_{drop-avg}$ directly, the potential difference can be maintained for a period of time sufficient to determine a current, $I_{pre-switch}$ prior to switching off the application potential or initiation of the switching cycles. The determined value of $I_{pre-witch}$ may be used to calculate track resistance, $R_{track}$ according to the formula $R_{track}=V_{drop}/I_{pre-switch}$ when only a single value of $V_{drop}$ is determined. Alternatively, when n switching cycles are performed, $R_{track}$ is given by the formula:

$$R_{track} = \frac{1}{n}\left(\sum_n V_{drop,n} / I_{pre-switch,n}\right), \text{ or}$$

$$R_{track} = \left(\frac{\sum_n V_{drop,n}}{\sum_n I_{pre-switch,n}}\right).$$

Medians and averages omitting outlines may also be used rather than arithmetic averages of all values. The determined value of $R_{track}$ is then compared to a predetermined range (which may be open-ended) and the reading is rejected if the value falls outside the range.

Use of $R_{track}$ rather than $V_{drop}$ or $V_{drop-avg}$ can give superior results, particularly in instances where the measured levels of analyte, and thus the magnitude of the voltage signal and the plateau current can be variable, since it tends to normalize the sample based effects on $V_{drop}$ or $V_{drop-avg}$ and make the correction process more robust.

Figure 10A:
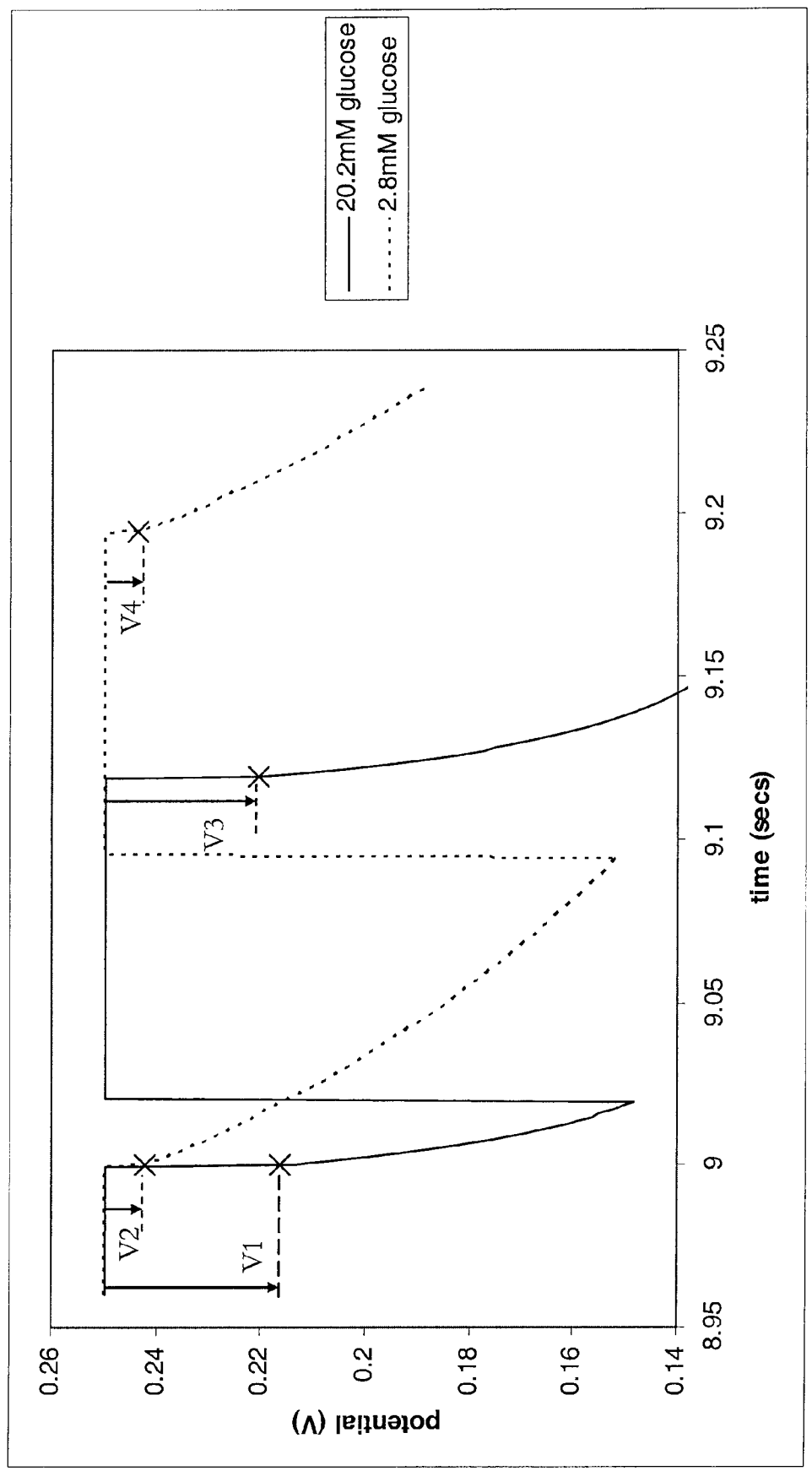
FIGS. 10A and 10B show potential versus time and current versus time in an example with 2 switching cycles.
Figure 10B:
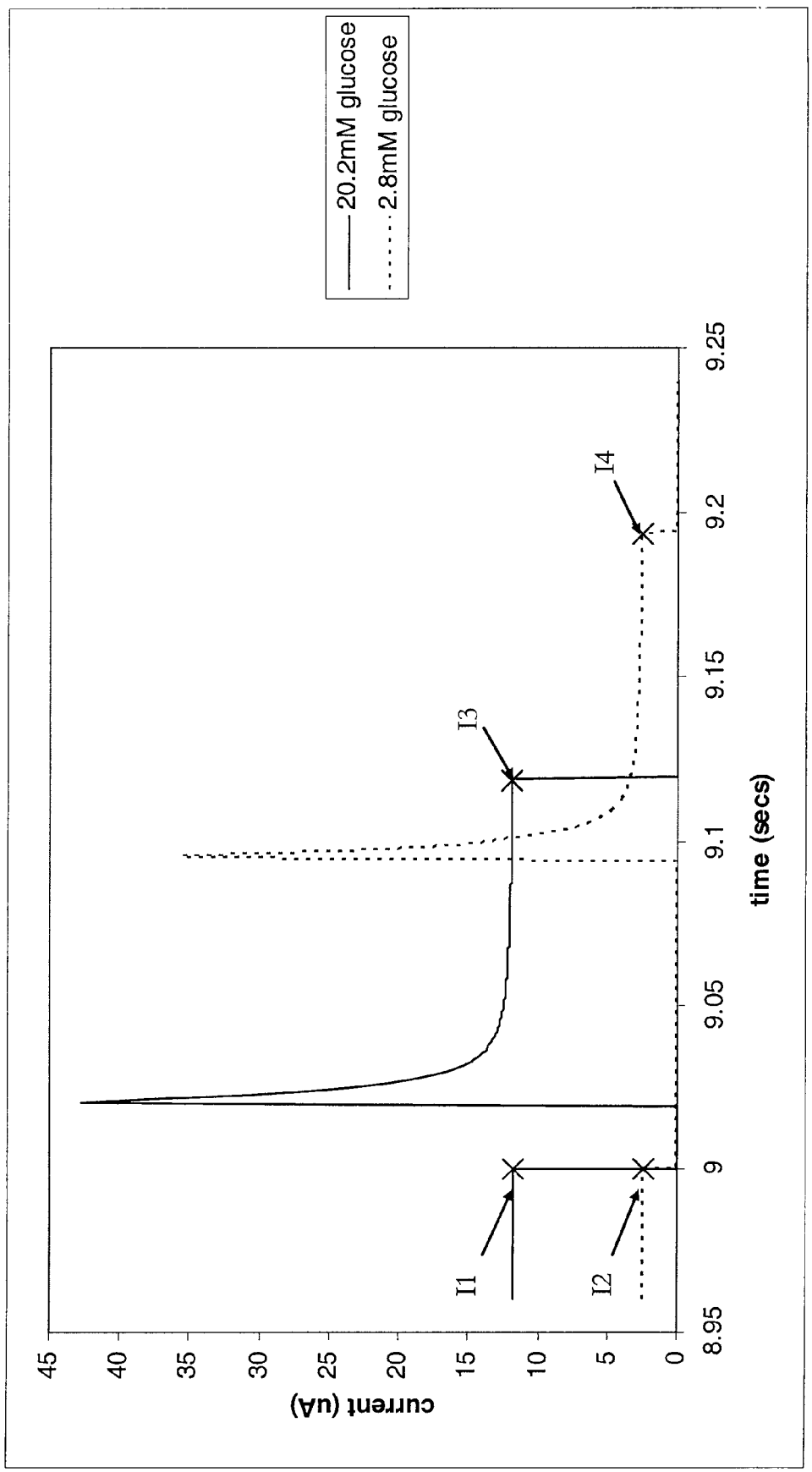

FIGS. 10A and 10B show potential versus time and current versus time in an example with 2 switching cycles for 2.8 mM and 20.2 mM glucose standards. Both figures begin at 8.95 seconds after first application of the potential difference, when the current 11, 12 is in the plateau region and the potential is switched on. At 9 seconds, the current is switched off, and the immediate drop in potential and current is observed. In the case of the 20.2 mM glucose (solid line) a large $V_{drop}$=V1 is observed followed by further decay of the potential over time. Thereafter, at approximately 9.02 seconds, the potential is reapplied, which results in a spike in the current followed by a decay to a plateau value. At about 9.12 seconds this potential is turned off, resulting in the second value for $V_{drop}$=V3. The sample with 2.8 mM glucose is handled in substantially the same way. The time intervals shown in the figures are longer for this sample but they could be the same. Specifically, the switching on of potential in the case of the 2.8 mM sample occurs at about 9.09 seconds and the switching off of the potential occurs at about 9.19 seconds.

VI. APPARATUS OF THE INVENTION

The method of the invention can be used with any strip that has a working and a counter electrodes, providing that a meter apparatus is provided that can receive the strip and provide the necessary applications of voltage and signal processing. Such a meter also forms an aspect of the present invention. Thus, the invention provides a meter for receiving an electrochemical test strip having working and counter electrodes and providing a determination of an analyte in a sample applied to the electrochemical test strip when received in the meter, said meter comprising (a) a housing having a slot for receiving an electrochemical test strip;

(b) communications means for receiving input from and communicating a result to a user; and (c) means for applying a potential and to determine analyte concentration from an observed current, (d) means for switching off the potential and determining $V_{drop}$;

(e) means for calculating $R_{track}$, and (f) means for comparing $R_{track}$ with a predetermined range and generating an error message in place of a result if $R_{track}$ falls outside the range.

The invention also provides a meter which comprises means for performing a plurality of switching cycles and calculating $V_{drop-avg}$ instead of merely determining $V_{drop}$ and optionally determining $R_{track}$ using $V_{drop}$ or $V_{drop-avg}$.

Figure 5:
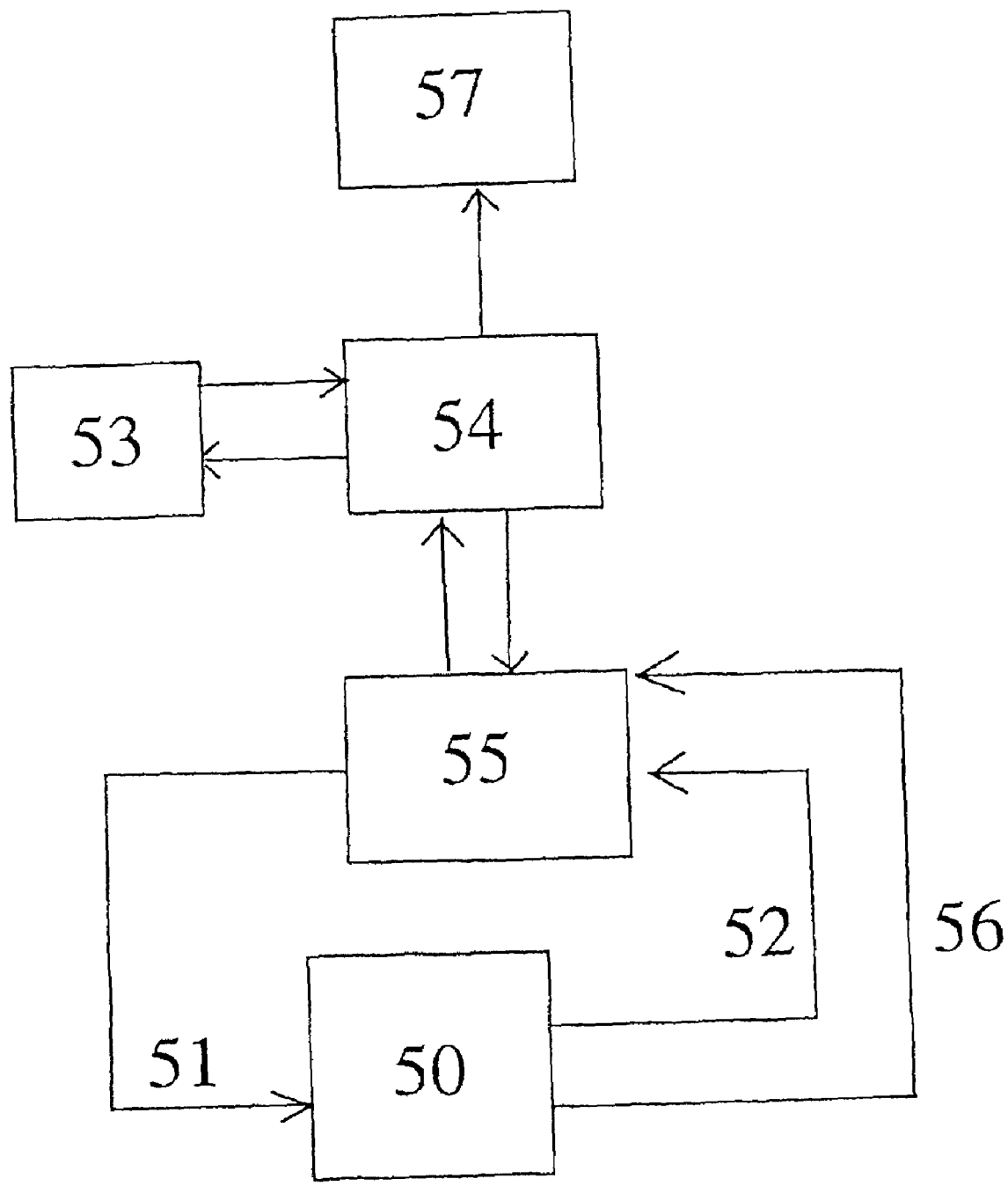
FIG. 5 illustrates the components of an embodiment of the invention schematically.

FIG. 5 illustrates the components of an embodiment of the invention schematically. As shown in FIG. 5, potential 51 is generated by circuit 55 and applied to a test strip 50. This results in a current signal 52 which is stored at 53. At time $t_{switch}$, microprocessor 54 causes circuit 55 to stop applying potential and to start monitoring the potential difference 56 in the test strip, and determine series electrode resistance. If the series electrode resistance falls outside the predetermined range of acceptable values, an error message is sent to display 57. Otherwise, the stored current data is retrieved from 53 and a result is determined and sent to display 57.

Figure 6:
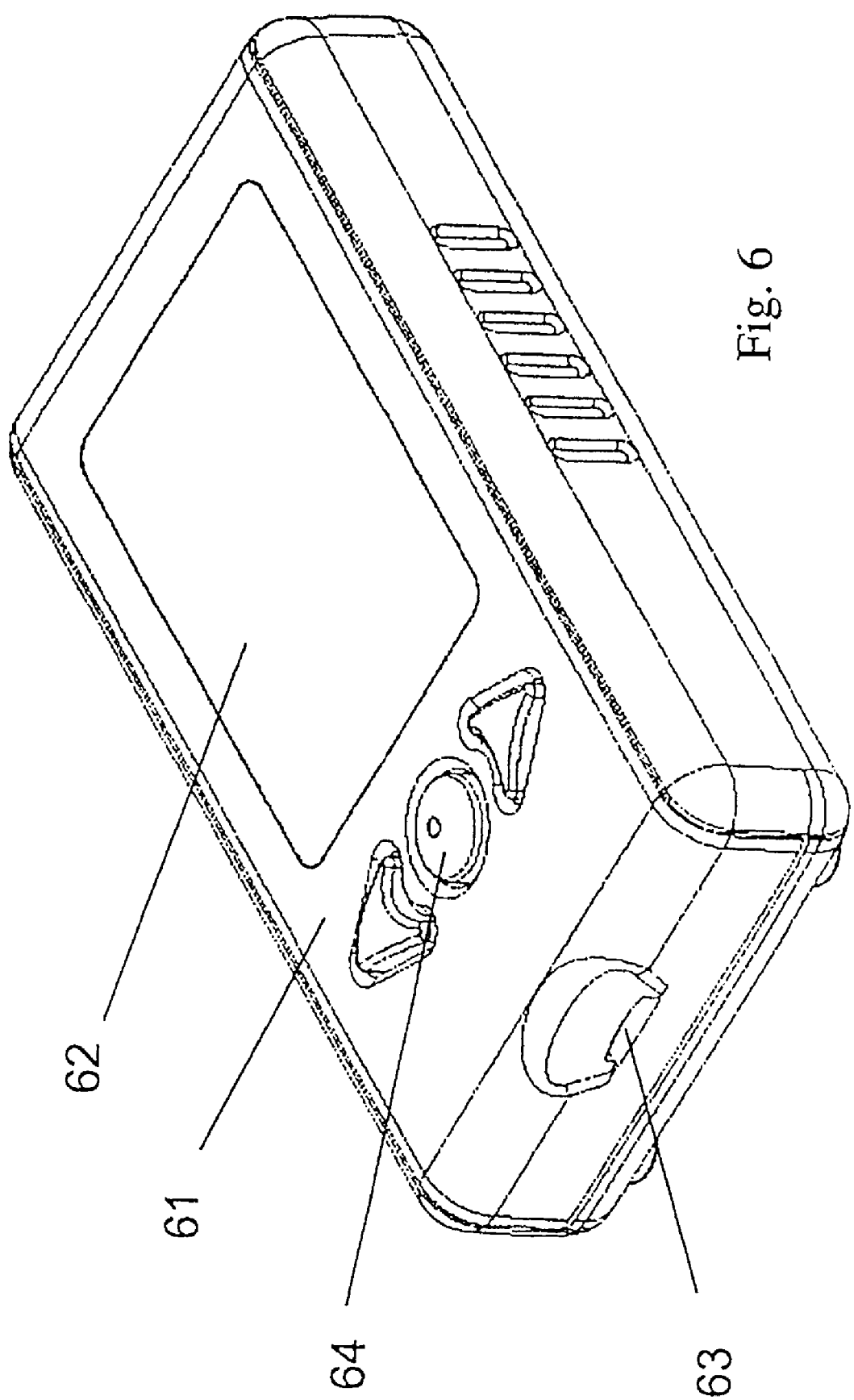
FIG. 6 shows an exterior view of a meter.

FIG. 6 shows an external view of a meter in accordance with the invention. The meter has a housing 61, and a display 62. The housing 61 has a slot 63, into which a test strip is inserted for use. The meter may also have a button 64 for signaling the start of the measurement cycle, or may have an internal mechanism for detecting the insertion of a test strip or the application of a sample. Such mechanisms are known in the art, for example from U.S. Pat. Nos. 5,266,179; 5,320, 732; 5,438,271 and 6,616,819, which are incorporated herein by reference. In the meter of the invention, buttons, displays such as LCD displays, RF, infrared or other wireless transmitters, wire connectors such as USB, parallel or serial connections constitute means for receiving input from and communicating a result to a user, and can be used individually and in various combinations.

Figure 7:
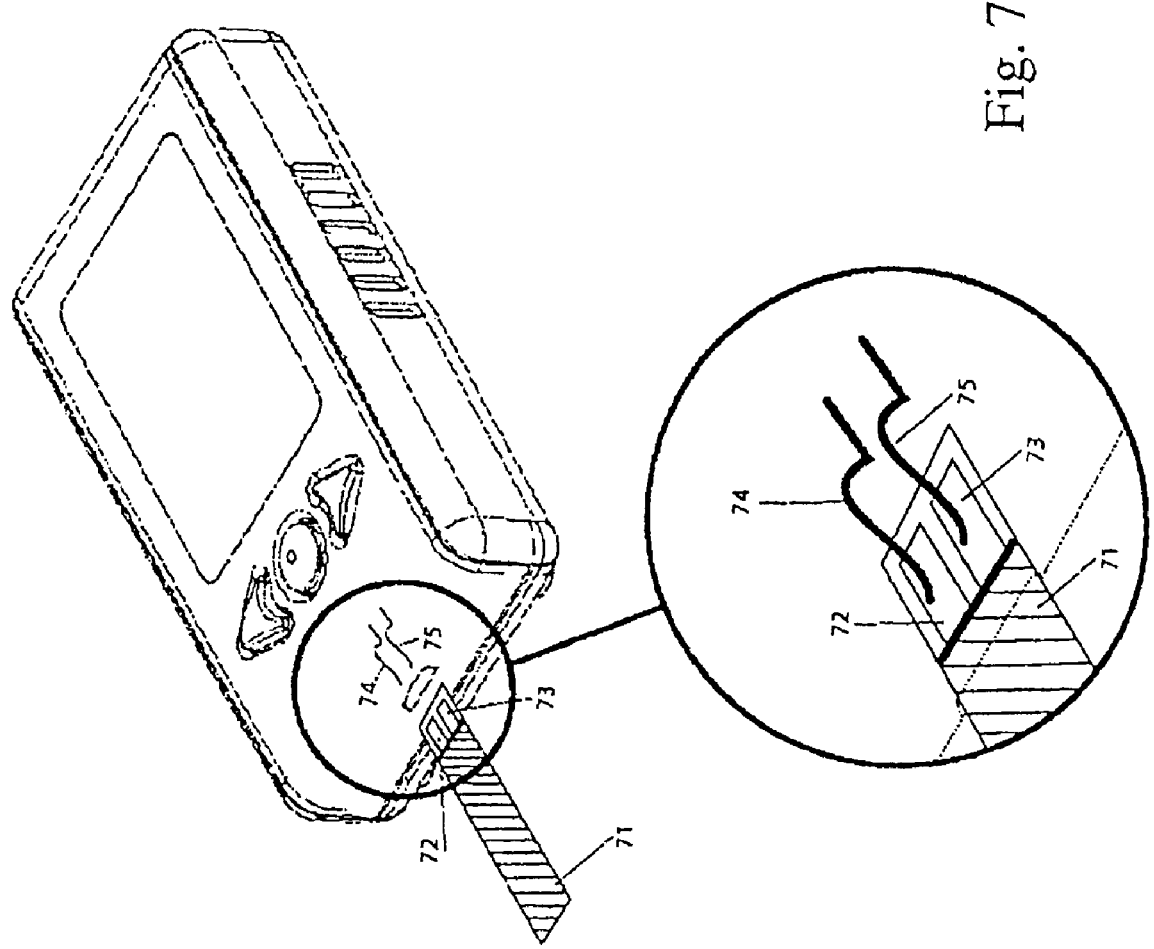
FIG. 7 shows connection of a test strip and connectors in a meter.

FIG. 7 shows an interior view in which the connection of the meter to a test strip is shown. As shown, the test strip 71 has contacts 72, 73 by which the electrodes are placed in electrical contact with contacts 74, 75 of the meter.

The means for applying a potential and to determine analyte concentration from an observed current, means for switching off the potential and determining $V_{drop}$; and means for comparing $V_{drop}$ with a predetermined range and generating an error message in place of a result if $V_{drop}$ falls outside the range comprises circuits, such as on a circuit board associated with a programmed microprocessor that interacts with the circuits to provide the desired switching between amperometric and potentiometric modes and to monitor current and voltage as described, and storage components such as flash memory, EEPROMS or battery backed RAM.

Apparatus suitable for switching between an amperometric mode of operation in which current is measured and a potentiometric mode of operation in which a potential difference between the electrodes is measured are described in U.S. Provisional Applications No. 60/521,592, filed May 30, 2004, and 60/594,285 filed Mar. 25, 2005, and U.S. patent application Ser. No. 10/907790, filed Apr. 15, 2005, which are incorporated herein by reference.

Figure 8:
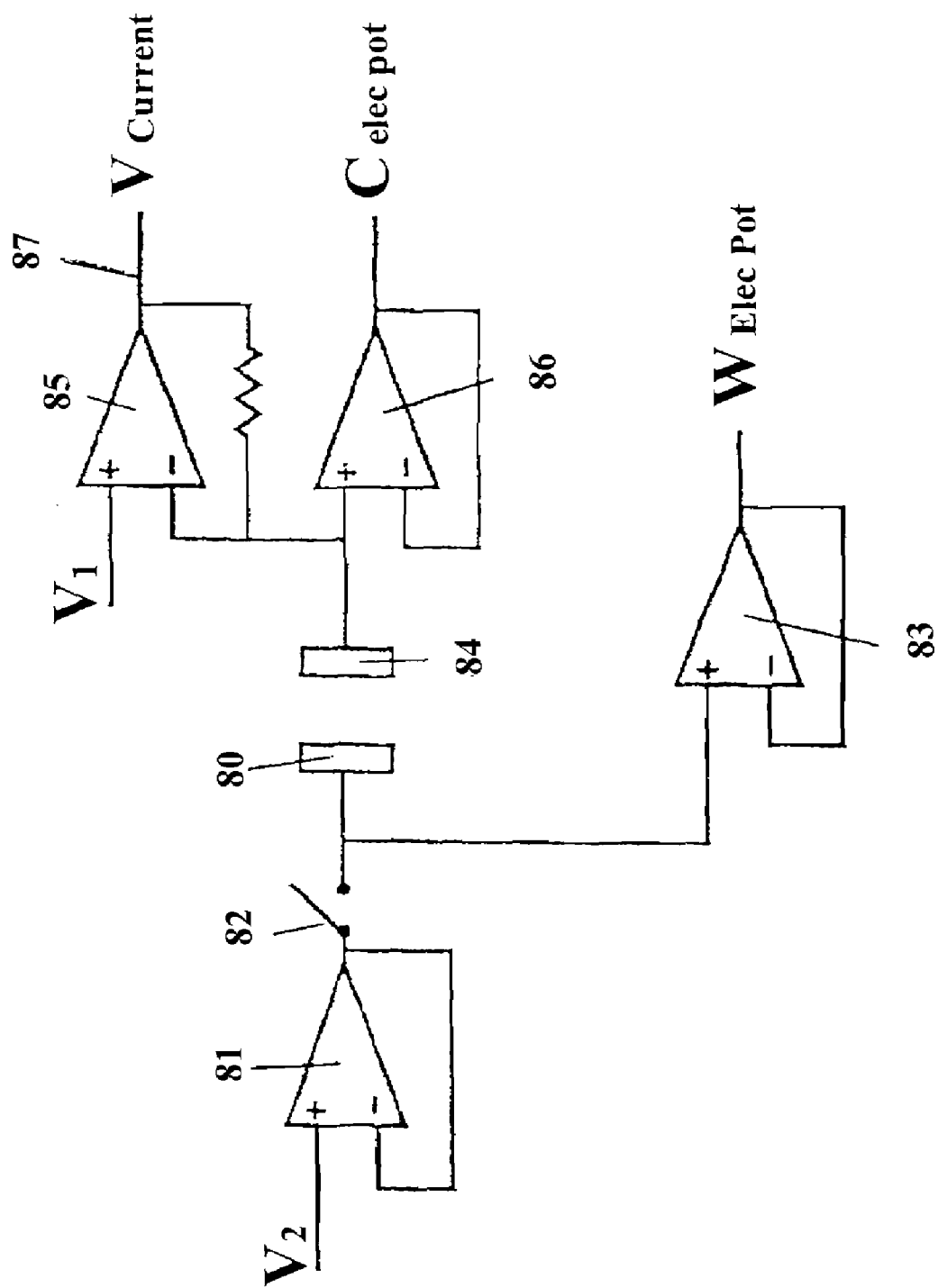
FIG. 8 shows a circuit diagram for switching between amperometric and potentiometric modes.

FIG. 8 shows an electrical schematic of a circuit useful as circuit 55 in FIG. 5. It will be appreciated, however, that other components can also be used, which achieve the same results in terms of applying and switching the voltage. Working electrode 80 is connected to op amp 81 via a connector containing switch 82, and to op amp 83. Counter electrode 84 is connected to op amps 85 and 86. Op amps 83, 85 and 86 are high impedance input amplifiers. When operating in amperometric mode to determine an analyte, a voltage $V_2$ is applied to op amp 81, and a voltage $V_1$ is applied to op amp 85, $V_2$ being greater than $V_1$. The resulting potential difference between the electrodes results in the generation of a current that is related to the amount of analyte, and this current can be monitored at output 87 and converted to an indication of the presence or amount of analyte. When switch 82 is opened to create an open circuit and stop application of the potential difference, current flow ceases, and the output of amplifier 86 assumes the potential of the counter electrode, while the output of amplifier 83 assumes the potential of the working electrode 80. The difference between the output from op amp 83 and op amp 86 indicates the decay in chemical potential and is processed in accordance with the methods described above to create an indication of partial fill.

Figure 9:
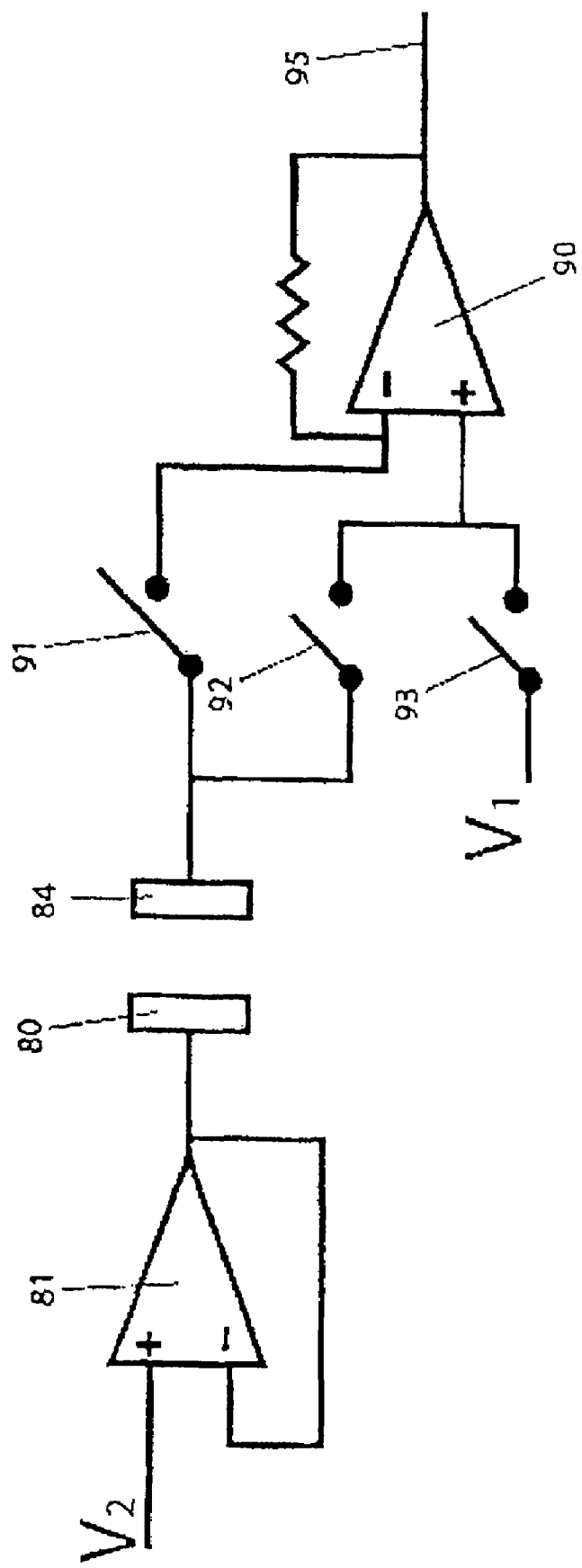
FIG. 9 shows a circuit diagram for switching between amperometric and potentiometric modes.

FIG. 9 shows an alternative version of this circuit using only two op amps and an increased number of switches. Working electrode 80 is connected to op amp 81 which received input voltage $V_2$. Counter electrode 84 is connected to high input impedance op amp 90 via one of two switched paths. Input voltage $V_1$ is connected to the circuit via a third switched path. When switch 91 and 93 are closed, and switch 92 is open, the circuit functions in amperometric mode, and the output at 95 reflects current flow at the electrodes. When switch 92 is closed, and switches 91 and 93 are open, the circuit operates in potentiometric mode and the output at 95 assumes the potential of the counter electrode (similar to amplifier 86 in FIG. 8). Thus, the output at 95 indirectly reflects the difference in potential between the electrodes. The actual difference in potential between the electrodes is the difference between the output at 95, and the output of op amp 81 (at 80, the working electrode).

VI. MEASUREMENT SYSTEM

In actual use, the meter described above is combined with an electrochemical test strip for the determination of a particular analyte, such as glucose. This combination, referred to as a measurement system, forms a further aspect of the present invention.

VII. EXAMPLE

To assess the relationship between strip damage and measured values of $V_{drop}$ two sets of test strips were evaluated. For data on "normal" cells, measurements were made using electrochemical test strips having facing screen printed carbon electrodes, a nominal sample volume of 625 nanoliters, and a viewing window. For data on damaged cells, the same type of strip was used, but a notch was cut into the side of the test strip creating a narrowed region in the working electrode track 41. (FIG. 4A).

Blood samples used in the tests were freshly drawn (less than 8 hours old) using Vacutainer™ tubes, and were stabilized with EDTA as an anticoagulant $V_{drop}$ was determined from Vapp-$V_{elect}$, with $V_{elect}$ being determined by extrapolating the potential decay using a linear approximation back to time $t_{switch}$.

FIG. 4B shows the determined values of $V_{drop}$ for damaged test strips (circles) and undamaged test strips (squares). Line A shows an appropriate threshold (open-ended range) for this test strip, which has a value of 130 mV.

What is claimed is:

1. A method for determination of an analyte in a sample comprising the steps of:
   (a) introducing the sample to an electrochemical test strip having working and counter electrodes;
   (b) applying a potential difference, $V_{app}$, between the electrodes of the test strip and observing a current signal sufficient to provide a determination of analyte in the sample and for a period of time sufficient to determine a plateau current, $I_{plateau}$, that reflects the recycling or shuttling of mediator between the electrodes;
   (c) switching off the applied potential at time $t_{switch}$ and determining the magnitude, $V_{drop}$, of a voltage drop arising from series electrode resistance, if present;
   (d) calculating a track resistance $R_{track}$, and comparing the determined magnitude of $R_{track}$ against a predetermined range, and rejecting the test if the magnitude of $R_{track}$ falls outside of the range wherein the value of $R_{track}=V_{drop}/I_{plateau}$; and
   (e) if the magnitude is within the predetermined range, proceeding to display or communicate the result from the determination of analyte.

2. The method of claim 1, wherein $V_{drop}$ is defined as the difference in potential between $V_{app}$ and the potential measured at a predetermined time after the potential is switched off.

3. The method of claim 1, wherein $V_{drop}$ is defined as the difference in potential between $V_{app}$ and the electrochemical potential, $V_{elect}$.

4. The method of claim 3, wherein $V_{elect}$ is determined by extrapolating voltage decay observed in a time interval after the potential is switched off when decrease in potential associated with series electrode resistance has occurred and determining the extrapolated value of potential at the time the potential was switched off.

5. The method of claim 4, wherein the time interval is from 0.5 to 2 milliseconds.

6. The method of claim 5, wherein the time interval is 1 millisecond.

7. A meter for receiving an electrochemical test strip having working and counter electrodes and providing a determination of an analyte in a sample applied to the electrochemical test strip when received in the meter, said meter comprising:
   (a) a housing having a slot for receiving an electrochemical test strip;
   (b) communications means for receiving input from and communicating a result to a user; and
   (c) means for applying a potential and to determine analyte concentration from an observed current and for measuring a plateau current, $I_{plateau}$;
   (d) means for switching off the potential at time $t_{switch}$ and determining $V_{drop}$;
   (e) means for calculating $R_{track}$; and
   (f) means for comparing $R_{track}$ with a predetermined range and generating an error message in place of a result if $R_{track}$ falls outside the range.

8. The meter of claim 7, wherein $V_{drop}$ is defined as the difference in potential between $V_{app}$ and the potential measured at a predetermined time after the potential is switched off.

9. The meter of claim 7, wherein $V_{drop}$ is defined as the difference between in potential between $V_{app}$ and the electrochemical potential, $V_{elect}$.

10. The meter of claim 9, wherein $V_{elect}$ is determined by extrapolating voltage decay observed in a time interval after the potential is switched off when decrease in potential associated with series electrode resistance has occurred and determining the extrapolated value of potential at time $t_{switch}$.

* * * * *